United States Patent
Kawamura (10) Patent No.: US 12,039,727 B2
(45) Date of Patent: Jul. 16, 2024

(54) ENERGY SUBTRACTION PROCESSING DEVICE, ENERGY SUBTRACTION PROCESSING METHOD, AND ENERGY SUBTRACTION PROCESSING PROGRAM

(71) Applicant: FUJIFILM CORPORATION, Tokyo (JP)

(72) Inventor: Takahiro Kawamura, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 369 days.

(21) Appl. No.: 17/673,734

(22) Filed: Feb. 16, 2022

(65) Prior Publication Data
US 2022/0172365 A1    Jun. 2, 2022

Related U.S. Application Data

(63) Continuation of application No. PCT/JP2020/032748, filed on Aug. 28, 2020.

(30) Foreign Application Priority Data

Sep. 18, 2019   (JP) ................ 2019-169025
Jul. 30, 2020   (JP) ................ 2020-129559

(51) Int. Cl.
    G06T 7/00     (2017.01)
    G06T 5/50     (2006.01)
    A61B 6/00     (2006.01)

(52) U.S. Cl.
CPC .......... G06T 7/0012 (2013.01); G06T 5/50 (2013.01); *A61B 6/482* (2013.01); *G06T 2207/30008* (2013.01)

(58) Field of Classification Search
CPC ........ G06T 7/0012; G06T 5/50; G06T 2207/30008; A61B 6/482
See application file for complete search history.

(56) References Cited

U.S. PATENT DOCUMENTS 6,125,166 A    9/2000   Takeo
2002/0085671 A1   7/2002   Sakaida
(Continued)

FOREIGN PATENT DOCUMENTS

JP    H11-205682 A    7/1999
JP    2000-232611 A    8/2000
(Continued)

OTHER PUBLICATIONS

Ito et al, "Improvement of Detection in Computed Radiography by New Single-Exposure Dual-Energy Subtraction", 1993, Journal of Digital ImagINg, vol. 6, No. 1, pp. 42-47 (6 Pages) (Year: 1993).*
(Continued)

*Primary Examiner* — David F Dunphy
(74) *Attorney, Agent, or Firm* — SOLARIS Intellectual Property Group, PLLC (57) ABSTRACT

An image acquisition unit acquires two radiographic images based on radiation which has different energy distributions and has been transmitted through a subject including a soft part and a bone part. A subtraction unit performs weighting subtraction using a predetermined initial weighting coefficient between corresponding pixels of the two radiographic images to derive a soft part image obtained by extracting the soft part of the subject and a bone part image obtained by extracting the bone part of the subject. A weighting coefficient derivation unit derives a new weighting coefficient on the basis of a pixel value of the bone part included in the bone part image. The subtraction unit performs the weighting subtraction on the two radiographic images using the new weighting coefficient to derive a new soft part image and a new bone part image.

10 Claims, 6 Drawing Sheets

(56) References Cited

U.S. PATENT DOCUMENTS

| | | | |
|---|---|---|---|
| 2012/0288062 A1 | 11/2012 | Takasaki | |
| 2015/0359502 A1* | 12/2015 | Zou | A61B 6/5235 378/101 |
| 2017/0000439 A1 | 1/2017 | Takasaki | |
| 2018/0028139 A1 | 2/2018 | Kuwabara | |
| 2018/0068442 A1* | 3/2018 | Kawamura | G06T 7/0012 |
| 2018/0279982 A1 | 10/2018 | Fukuda | |

FOREIGN PATENT DOCUMENTS

| | | | |
|---|---|---|---|
| JP | 2002-152593 A | 5/2002 | |
| JP | 2011-152280 A | 8/2011 | |
| JP | 2013-046774 A | 3/2013 | |
| JP | 2018-015453 A | 2/2018 | |
| JP | 2018-038646 A | 3/2018 | |
| JP | 2018-068800 A | 5/2018 | |
| JP | 2018-166652 A | 11/2018 | |
| WO | 2009/004678 A1 | 1/2009 | |

OTHER PUBLICATIONS

English language translation of the following: Office action dated Dec. 6, 2022 from the JPO in a Japanese patent application No. 2021-546577 corresponding to the instant patent application.
International Search Report issued in International Application No. PCT/JP2020/032748 on Oct. 6, 2020.
Written Opinion of the ISA issued in International Application No. PCT/JP2020/032748 on Oct. 6, 2020.

* cited by examiner

ENERGY SUBTRACTION PROCESSING DEVICE, ENERGY SUBTRACTION PROCESSING METHOD, AND ENERGY SUBTRACTION PROCESSING PROGRAM

CROSS REFERENCE TO RELATED APPLICATIONS

The present application is a Continuation of PCT International Application No. PCT/JP2020/032748, filed on Aug. 28, 2020, which claims priority to Japanese Patent Application No. 2019-169025, filed on Sep. 18, 2019 and Japanese Patent Application No. 2020-129559, filed on Jul. 30, 2020. Each application above is hereby expressly incorporated by reference, in its entirety, into the present application.

BACKGROUND

Technical Field

The present disclosure relates to an energy subtraction processing device, an energy subtraction processing method, and an energy subtraction processing program.

Related Art

In the related art, an energy subtraction process is known which uses two radiographic images obtained by irradiating a subject with two types of radiation having different energy distributions, using the fact that the amount of attenuation of the transmitted radiation varies depending on a substance constituting the subject. The energy subtraction process is a method which makes pixels of the two radiographic images obtained as described above correspond to each other, multiplies the corresponding pixels by an appropriate weighting coefficient, and performs subtraction to acquire an image obtained by extracting a specific structure. In a case in which the energy subtraction process is performed to derive a soft part image obtained by extracting a soft part from, for example, a radiographic image acquired by imaging the chest, it is possible to observe shadows that appear in the soft part without being disturbed by a bone part. On the contrary, in a case in which a bone part image obtained by extracting a bone part is derived, it is possible to observe shadows that appear in the bone part without being disturbed by the soft part.

In addition, a method has been proposed which acquires bone mineral content used to diagnose a bone-based disease, such as osteoporosis, using a bone part image acquired by the energy subtraction process. For example, JP2018-15453A discloses a radiography apparatus which comprises two radiation detectors that include a plurality of pixels accumulating charge corresponding to the emitted radiation and are disposed to be stacked. Further, a technique is known which measures the bone mineral content of a subject using each electric signal corresponding to the dose of radiation emitted to each radiation detector in this type of radiography apparatus.

However, in a case in which the energy subtraction process is performed, weighting coefficients for two radiographic images acquired by radiation having different energy distributions are derived on the basis of the attenuation coefficients of the soft part and the bone part for the radiation having different energy distributions. Here, the substance has a radiation attenuation coefficient depending on the energy of the radiation. On the other hand, in a case in which the radiation emitted to the subject is not monochromatic, but is distributed in a certain energy range, a so-called beam hardening phenomenon occurs in which the energy distribution of the detected radiation changes depending on the thickness of the substance (a bone part and a soft part in the case of the human body) included in the subject. That is, the attenuation coefficient depends on the energy of the radiation. The attenuation coefficient has the characteristic that, as the energy of a component becomes higher, the attenuation coefficient becomes smaller. Therefore, the radiation loses a relatively large number of low-energy components while passing through the substance, and the proportion of high-energy components increases. This phenomenon is beam hardening. Therefore, in a case in which the weighting coefficient is derived, an attenuation coefficient obtained by weighting the radiation attenuation coefficient of the substance with the detected radiation energy distribution and averaging the weighted radiation attenuation coefficient is used. In addition, the average attenuation coefficient varies depending on the thickness of the sub stance.

Here, the attenuation coefficient for deriving the weighting coefficient used in a case in which the energy subtraction process is performed is calculated by, for example, presumption on the basis of a low-energy image acquired by low-energy radiation having a low energy distribution. Therefore, in a case in which the energy subtraction process is performed, the same attenuation coefficient is used as the weighting coefficient in all of the pixels. However, the thickness of the substance in the subject varies depending on the location of the subject. Further, as described above, the attenuation coefficient varies depending on the thickness of the substance in the subject. Therefore, for example, in a case in which the subject is a human body, the thickness of the soft part and the bone part is not constant depending on the part. In a case in which the same attenuation coefficient is used as the weighting coefficient in all of the pixels, it is difficult to completely remove an unnecessary structure in a difference image. As a result, there is a problem that the bone part remains in the soft part image and the soft part remains in the bone part image.

Therefore, a method has been proposed which calculates in advance a relationship between a difference between the logarithmic values of radiation doses of pixels in two radiographic images acquired by radiation having different energy distributions or a ratio or difference between the radiation doses of the pixels in the two radiographic images and an attenuation coefficient that is used as a weighting coefficient in a case in which a subtraction process is performed, derives the attenuation coefficient with reference to the relationship, and performs the subtraction process using the derived attenuation coefficient as the weighting coefficient (see JP2002-152593A). The ratio or difference between the radiation doses used in the method described in JP2002-152593A reflects the influence of beam hardening caused by the difference in the thickness of the subject, and the weighting coefficient is calculated according to the degree of beam hardening. Therefore, according to the method described in JP2002-152593A, it is possible to obtain a difference image obtained by appropriately extracting the soft part and the bone part, that is, a soft part image and a bone part image in consideration of the influence of the beam hardening.

However, for the ratio or difference between the radiation doses in the method described in JP2002-152593A, it is not considered that the attenuation characteristics of the radiation vary depending on the composition (the soft part and the bone part) constituting the body of the subject. Therefore, in the method described in JP2002-152593A, the weighting coefficient may not be optimal in a case in which a composition ratio is different. In addition, since the energy characteristics of the radiation source and the sensitivity characteristics of the radiation detector change over time, the difference or ratio between the radiation doses is likely to be affected by a change in the imaging apparatus over time. Therefore, even in a case in which the weighting coefficient derived by the method described in JP2002-152593A is used, it is difficult to separate tissues with high accuracy. Therefore, there is a concern that an unnecessary structure will be included in the difference image.

SUMMARY OF THE INVENTION

The present disclosure has been made in view of the above circumstances, and an object of the present disclosure is to provide a technique that can remove an unnecessary structure in a difference image derived by an energy subtraction process with high accuracy.

According to the present disclosure, there is provided an energy subtraction processing device comprising: an image acquisition unit that acquires two radiographic images based on radiation which has different energy distributions and has been transmitted through a subject including a soft part and a bone part; a subtraction unit that performs weighting subtraction using a predetermined initial weighting coefficient between corresponding pixels of the two radiographic images to derive a soft part image obtained by extracting the soft part of the subject and a bone part image obtained by extracting the bone part of the subject; and a weighting coefficient derivation unit that derives a new weighting coefficient on the basis of a pixel value of the bone part included in the bone part image. The subtraction unit performs the weighting subtraction on the two radiographic images using the new weighting coefficient to derive a new soft part image and a new bone part image.

In addition, in the energy subtraction processing device according to the present disclosure, the weighting coefficient derivation unit may derive the new weighting coefficient on the basis of a predetermined relationship between the pixel value of the bone part and the weighting coefficient.

Further, in the energy subtraction processing device according to the present disclosure, the weighting coefficient derivation unit may correct the new weighting coefficient on the basis of a pixel value of a bone part included in the new bone part image to derive a further new weighting coefficient. The subtraction unit may perform the weighting subtraction using the further new weighting coefficient to derive a further new soft part image and a further new bone part image. The derivation of the further new weighting coefficient based on the new bone part image and the derivation of the further new soft part image and the further new bone part image based on the new weighting coefficient may be repeated to derive the weighting coefficient, the soft part image, and the bone part image.

Furthermore, the energy subtraction processing device according to the present disclosure may further comprise a scattered ray removal unit that removes scattered ray components included in the two radiographic images. The subtraction unit may perform the weighting subtraction on the basis of the two radiographic images from which the scattered ray components have been removed.

Moreover, in the energy subtraction processing device according to the present disclosure, the scattered ray removal unit may remove the scattered ray components included in the two radiographic images on the basis of radiation characteristics of an object interposed between the subject and detection units that acquire the two radiographic images.

In addition, in the energy subtraction processing device according to the present disclosure, two detection units that are superimposed on each other may be irradiated with the radiation transmitted through the subject at the same time to acquire the two radiographic images.

Further, the energy subtraction processing device according to the present disclosure may further comprise an initial weighting coefficient setting unit that sets the initial weighting coefficient on the basis of a body thickness of the subject.

In this case, the energy subtraction processing device may further comprise a body thickness derivation unit that derives the body thickness of the subject.

According to the present disclosure, there is provided an energy subtraction processing method comprising: acquiring two radiographic images based on radiation which has different energy distributions and has been transmitted through a subject including a soft part and a bone part; performing weighting subtraction using a predetermined initial weighting coefficient between corresponding pixels of the two radiographic images to derive a soft part image obtained by extracting the soft part of the subject and a bone part image obtained by extracting the bone part of the subject; deriving a new weighting coefficient on the basis of a pixel value of the bone part included in the bone part image; and performing the weighting subtraction on the two radiographic images using the new weighting coefficient to derive a new soft part image and a new bone part image.

In addition, a program that causes a computer to perform the energy subtraction processing method according to the present disclosure may be provided.

Another energy subtraction processing device according to the present disclosure comprises a memory that stores commands to be executed by a computer and a processor configured to execute the stored commands. The processor performs a process including: acquiring two radiographic images based on radiation which has different energy distributions and has been transmitted through a subject including a soft part and a bone part; performing weighting subtraction using a predetermined initial weighting coefficient between corresponding pixels of the two radiographic images to derive a soft part image obtained by extracting the soft part of the subject and a bone part image obtained by extracting the bone part of the subject; deriving a new weighting coefficient on the basis of a pixel value of the bone part included in the bone part image; and performing the weighting subtraction on the two radiographic images using the new weighting coefficient to derive a new soft part image and a new bone part image.

According to the present disclosure, it is possible to remove an unnecessary structure in the difference image derived by the energy subtraction process with higher accuracy, without being affected by the deterioration of the imaging apparatus over time.

DETAILED DESCRIPTION

Figure 1:
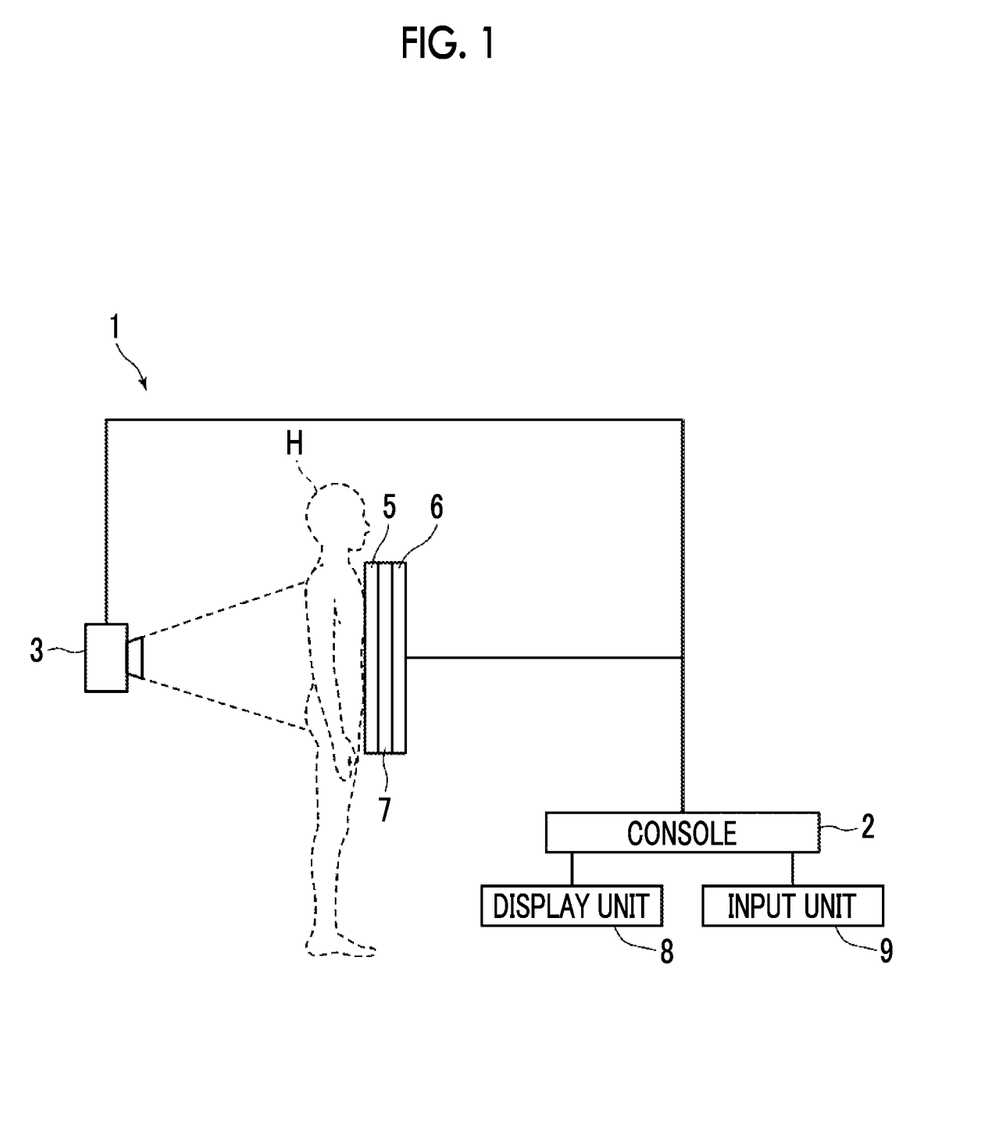
FIG. 1 is a diagram schematically illustrating a configuration of a radiography system to which an energy subtraction processing device according to an embodiment of the present disclosure is applied.

Hereinafter, embodiments of the present disclosure will be described with reference to the drawings. FIG. 1 is a block diagram schematically illustrating a configuration of a radiography system to which an energy subtraction processing device according to an embodiment of the present disclosure is applied. As illustrated in FIG. 1, the radiography system according to this embodiment captures two radiographic images having different energy distributions, performs an energy subtraction process using the two radiographic images, and comprises an imaging apparatus 1 and a console 2 including the energy subtraction processing device according to this embodiment.

The imaging apparatus 1 is an imaging apparatus for performing so-called one-shot energy subtraction that irradiates each of a first radiation detector 5 and a second radiation detector 6 with radiation, such as an X-ray, which has been emitted from a radiation source 3 and transmitted through a subject H, while changing energy. At the time of imaging, as illustrated in FIG. 1, the first radiation detector 5, a radiation energy conversion filter 7 that consists of, for example, a copper plate, and the second radiation detector 6 are disposed in this order from the side closer to the radiation source 3, and the radiation source 3 is driven. In addition, the first and second radiation detectors 5 and 6 and the radiation energy conversion filter 7 are closely attached to each other.

With this configuration, the first radiation detector 5 acquires a first radiographic image G1 of the subject H obtained by low-energy radiation including so-called soft rays. Further, the second radiation detector 6 acquires a second radiographic image G2 of the subject H obtained by high-energy radiation excluding soft rays. The first and second radiographic images are input to the console 2. In addition, in this embodiment, in a case in which the subject H is imaged, a scattered ray removal grid that removes a scattered ray component of the radiation transmitted through the subject H is not used. Therefore, the first radiographic image G1 and the second radiographic image G2 include a primary ray component and a scattered ray component of the radiation transmitted through the subject H.

The first and second radiation detectors 5 and 6 can repeatedly perform the recording and reading of a radiographic image and may be a so-called direct-type radiation detector that directly receives the emitted radiation and generates charge or a so-called indirect-type radiation detector that converts radiation into visible light and then converts the visible light into a charge signal. In addition, as a method for reading a radiographic image signal, it is desirable to use a so-called thin film transistor (TFT) reading method which turns on and off a TFT switch to read out a radiographic image signal or a so-called optical reading method which emits reading light to read out a radiographic image signal. However, the present disclosure is not limited thereto, and other methods may be used.

A display unit 8 and an input unit 9 are connected to the console 2. The display unit 8 consists of a display, such as a cathode ray tube (CRT) or a liquid crystal display, and assists the input of radiographic images acquired by imaging, a soft part image and a bone part image, which will be described below, and various kinds of information necessary for processes performed in the console 2.

The input unit 9 consists of a keyboard, a mouse, or a touch-panel-type input device and receives instructions to operate the imaging apparatus 1 from an operator. In addition, the input unit 9 receives the input of various kinds of information required for imaging, such as imaging conditions, and an instruction to correct information. In this embodiment, each unit of the imaging apparatus 1 is operated according to the information input by the operator through the input unit 9.

An energy subtraction processing program according to this embodiment is installed in the console 2. The console 2 corresponds to the energy subtraction processing device according to this embodiment. In this embodiment, the console 2 may be a workstation or a personal computer that is directly operated by the operator or a server computer that is connected to them through a network. The energy subtraction processing program is stored in a storage device of the server computer connected to the network or a network storage in a state in which it can be accessed from the outside and is downloaded and installed in the computer as required. Alternatively, the energy subtraction processing program is recorded on a recording medium, such as a digital versatile disc (DVD) or a compact disc read only memory (CD-ROM), is distributed, and is installed in the computer from the recording medium.

Figure 2:
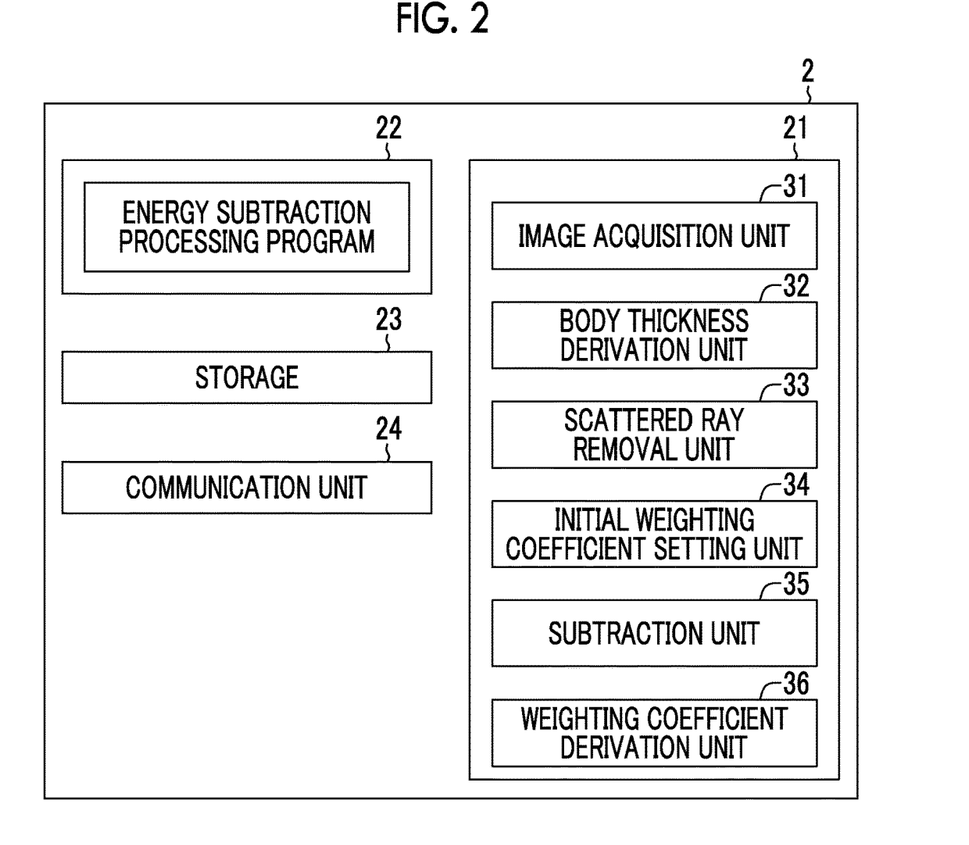
FIG. 2 is a diagram illustrating a schematic configuration of the energy subtraction processing device according to this embodiment.

FIG. 2 is a diagram illustrating a schematic configuration of the energy subtraction processing device implemented by installing the energy subtraction processing program in the computer constituting the console 2. As illustrated in FIG. 2, the energy subtraction processing device comprises a central processing unit (CPU) 21, a memory 22, a storage 23, and a communication unit 24 as a standard computer configuration.

The storage 23 consists of a storage device, such as a hard disk drive or a solid state drive (SSD), and stores various kinds of information including a program for driving each unit of the imaging apparatus 1 and the energy subtraction processing program. In addition, the radiographic image acquired by imaging is stored in the storage 23.

The communication unit 24 is a network interface that controls the transmission of various kinds of information to an external device through the network (not illustrated).

The memory 22 temporarily stores, for example, the program stored in the storage 23 in order to cause the CPU 21 to perform various processes. The energy subtraction processing program defines, as processes performed by the CPU 21, an image acquisition process of directing the imaging apparatus 1 to perform imaging to acquire the first and second radiographic images G1 and G2 having different energy distributions, a body thickness derivation process of deriving the body thickness of the subject H, a scattered ray removal process of removing scattered ray components included in the first and second radiographic images G1 and G2, an initial weighting coefficient setting process of setting an initial weighting coefficient, which is an initial value of a weighting coefficient in a case in which a subtraction process which will be described below is performed, on the basis of the body thickness of the subject H, the subtraction process of performing weighting subtraction using the initial weighting coefficient between the corresponding pixels of the first and second radiographic images G1 and G2 to derive a soft part image obtained by extracting a soft part of the subject H and a bone part image obtained by extracting a bone part of the subject H, and a weighting coefficient derivation process of deriving a new weighting coefficient on the basis of the pixel value of the bone part included in the bone part image.

Then, the CPU 21 performs these processes according to the energy subtraction processing program such that the console 2 functions as an image acquisition unit 31, a body thickness derivation unit 32, a scattered ray removal unit 33, an initial weighting coefficient setting unit 34, a subtraction unit 35, and a weighting coefficient derivation unit 36.

The image acquisition unit 31 drives the radiation source 3 to irradiate the subject H with radiation, detects the radiation transmitted through the subject H using the first and second radiation detectors 5 and 6, and acquires the first and second radiographic images G1 and G2. In this case, imaging conditions, such as an imaging dose, an energy distribution, a tube voltage, and a SID, are set. The imaging conditions may be set by an input operation of the operator through the input unit 9. The set imaging conditions are stored in the storage 23. In addition, the first and second radiographic images G1 and G2 may be acquired by a program different from the energy subtraction processing program and then stored in the storage 23. In this case, the image acquisition unit 31 reads out the first and second radiographic images G1 and G2 stored in the storage 23 from the storage 23 in order to process the first and second radiographic images G1 and G2. Further, in this embodiment, it is assumed that the subject H is imaged from the chest to the abdomen and the first and second radiographic images G1 and G2 from the chest to the abdomen are acquired.

The body thickness derivation unit 32 derives the body thickness of the subject H for each pixel of the first and second radiographic images G1 and G2 on the basis of at least one of the first radiographic image G1 or the second radiographic image G2. Since the body thickness is derived for each pixel of the first and second radiographic images G1 and G2, the body thickness derivation unit 32 derives a body thickness distribution in at least one of the first radiographic image G1 or the second radiographic image G2. In a case in which the body thickness is derived, the body thickness derivation unit 32 uses the first radiographic image G1 acquired by the radiation detector 5 closer to the subject H. However, the second radiographic image G2 may be used. Further, even in a case in which any one of the images is used, a low-frequency image indicating a low-frequency component of the image may be derived, and the body thickness may be derived using the low-frequency image.

In this embodiment, assuming that a brightness distribution in the first radiographic image G1 is matched with the distribution of the body thickness of the subject H, the body thickness derivation unit 32 converts the pixel value of the first radiographic image G1 into a thickness using an attenuation coefficient in the soft part of the subject H to derive the body thickness of the subject H. Instead of this, the body thickness derivation unit 32 may measure the body thickness of the subject H using, for example, a sensor. In addition, the body thickness derivation unit 32 may approximate the body thickness of the subject H with a model, such as a cube or an elliptical column, to derive the body thickness. Further, the body thickness derivation unit 32 may derive the body thickness of the subject H using any method such as the method described in, for example, JP2015-043959A.

The scattered ray removal unit 33 removes the scattered ray components which are generated by the scattering of the radiation in the subject and are included in the first and second radiographic images G1 and G2. As a method for removing the scattered ray components, for example, any methods described in JP2014-207958A, JP2015-043959A, and the like can be used. The method described in JP2014-207958A acquires the characteristics of a grid that is assumed to be used to remove scattered rays in a case in which a radiographic image is captured, derives scattered ray components included in the radiographic image on the basis of the characteristics, and performs a scattered ray removal process using the derived scattered ray components. The method described in JP2015-043959A derives scattered ray components using the derived body thickness and performs a scattered ray removal process on the radiographic image. In addition, in the following description, it is assumed that G1 and G2 are used as reference numerals for the first and second radiographic images from which the scattered ray components have been removed, respectively.

Here, the removal of scattered rays in a case in which the method described in JP2015-043959A is used will be described. In a case in which, for example, the method described in JP2015-043959A is used, the derivation of the body thickness and the derivation of scattered ray components for removing scattered rays, which will be described below, are performed at the same time. Therefore, the derivation of the body thickness and the removal of the scattered rays are performed in the body thickness derivation unit 32 and the scattered ray removal unit 33 as follows. First, the body thickness derivation unit 32 and the scattered ray removal unit 33 acquire a virtual model of the subject H having an initial body thickness distribution and derive an estimated primary ray image which is obtained by estimating a primary ray image obtained by imaging the virtual model and an estimated scattered ray image which is obtained by estimating a scattered ray image obtained by imaging the virtual model. Further, in this embodiment, it is assumed that the estimated primary ray image and the estimated scattered ray image are derived using the first radiographic image G1. Then, the body thickness derivation unit 32 and the scattered ray removal unit 33 add the estimated primary ray image and the estimated scattered ray image to derive an estimated image. Furthermore, the body thickness derivation unit 32 and the scattered ray removal unit 33 correct the initial body thickness distribution such that a difference between the estimated image and the first radiographic image G1 is reduced.

Then, the body thickness derivation unit 32 and the scattered ray removal unit 33 derive an estimated image using the corrected body thickness distribution and repeat the generation of the estimated image using the corrected body thickness distribution and the correction of the body thickness distribution until the difference between the estimated image and the first radiographic image G1 satisfies a predetermined end condition. The body thickness derivation unit 32 derives, as the body thickness of the subject H, the body thickness distribution in a case in which the end condition is satisfied. The scattered ray removal unit 33 subtracts the estimated scattered ray image in a case in which the end condition is satisfied from the first radiographic image G1 to remove the scattered ray components from the first radiographic image G1. In addition, the scattered ray removal unit 33 derives an estimated scattered ray image for the second radiographic image G2 using the same method as that for the first radiographic image G1 and subtracts the derived estimated scattered ray image from the second radiographic image G2 to remove the scattered ray components from the second radiographic image G2.

The initial weighting coefficient setting unit 34 sets the initial weighting coefficient, which is the initial value of the weighting coefficient in a case in which the subtraction unit 35 performs the subtraction process, on the basis of the body thickness of the subject H derived by the body thickness derivation unit 32. Here, in this embodiment, the subtraction unit 35 performs the subtraction process of performing weighting subtraction between the corresponding pixels of the first and second radiographic images G1 and G2, from which the scattered ray components have been removed, using the initial weighting coefficient set by the initial weighting coefficient setting unit 34 and the weighting coefficient derived by the weighting coefficient derivation unit 36, to derive a soft part image Gs obtained by extracting the soft part of the subject H and a bone part image Gb obtained by extracting the bone part of the subject H, as represented by the following Expressions (1) and (2). In Expressions (1) and (2), α and β are weighting coefficients.

$$Gs(x,y) = \alpha \cdot G2(x,y) - G1(x,y) \quad (1)$$

$$Gb(x,y) = \beta \cdot G2(x,y) - G1(x,y) \quad (2)$$

Figure 3:
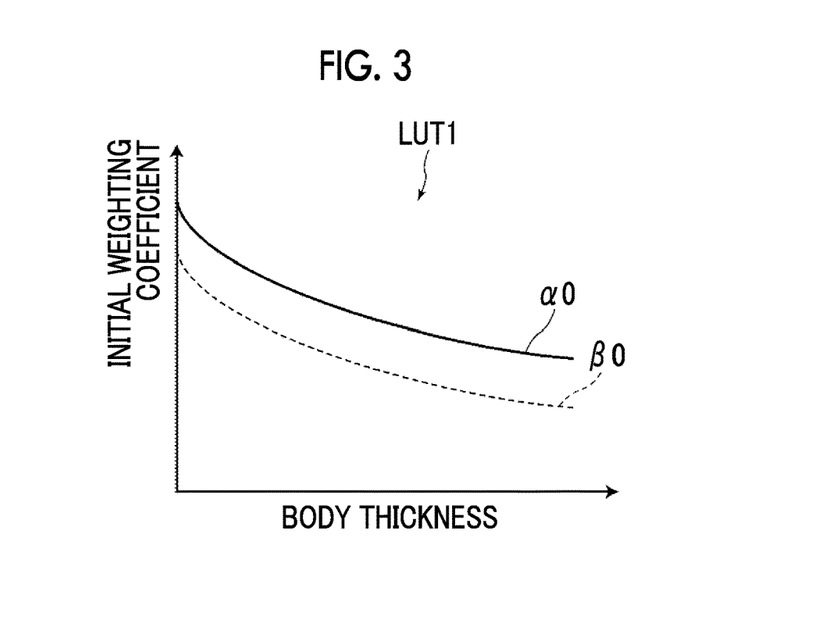
FIG. 3 is a diagram illustrating a table that defines a relationship between a body thickness and an initial weighting coefficient.

The initial weighting coefficient setting unit 34 sets initial weighting coefficients α0 and β0 which are the initial values of the weighting coefficients α and β on the basis of the body thickness derived by the body thickness derivation unit 32. In this embodiment, as illustrated in FIG. 3, a table LUT1 that defines the relationship between the body thickness and the initial weighting coefficients α0 and β0 is stored in the storage 23. The initial weighting coefficient setting unit 34 sets the initial weighting coefficients α0 and β0 on the basis of the body thickness with reference to the table LUT1.

Here, the relationship between the weighting coefficients α and β and a radiation attenuation coefficient will be described. Here, the radiation emitted from the radiation source 3 has an energy distribution. The attenuation coefficient also depends on the energy of the radiation. The radiation has the characteristic that, as the energy of a component becomes higher, the attenuation coefficient becomes smaller. Therefore, a so-called beam hardening phenomenon occurs in which radiation loses a relatively large number of low-energy components while passing through a substance and the proportion of high-energy components increases. Since the degree of beam hardening depends on a thickness ts of the soft part and a thickness tb of the bone part in the subject H, an attenuation coefficient μs of the soft part and an attenuation coefficient μb of the bone part can be defined as μs(ts, tb) and μb(ts, tb) as functions of ts and tb, respectively.

In the energy subtraction process, there are images having two different energy distributions. Therefore, in the low-energy image (the first radiographic image G1 in this embodiment), the attenuation coefficient of the soft part can be represented by μls(ts, tb), and the attenuation coefficient of the bone part can be represented by μlb(ts, tb). Further, in the high-energy image (the second radiographic image G2 in this embodiment), the attenuation coefficient of the soft part can be represented by μhs(ts, tb), and the attenuation coefficient of the bone part can be represented by μhb(ts, tb).

It is necessary to eliminate the contrast of the bone part included in the radiographic image in order to derive the soft part image Gs. Therefore, the weighting coefficient α can be calculated by α=μlb(ts, tb)/μhb(ts, tb) using the ratio of the attenuation coefficients of the bone part. Further, it is necessary to eliminate the contrast of the soft part included in the radiographic image in order to derive the bone part image Gb. Therefore, the weighting coefficient β can be calculated by β=μls(ts, tb)/μhs(ts, tb) using the ratio of the attenuation coefficients of the soft part. That is, the weighting coefficients α and β can be expressed as a function of the thickness is of the soft part and the thickness tb of the bone part.

Figure 4:
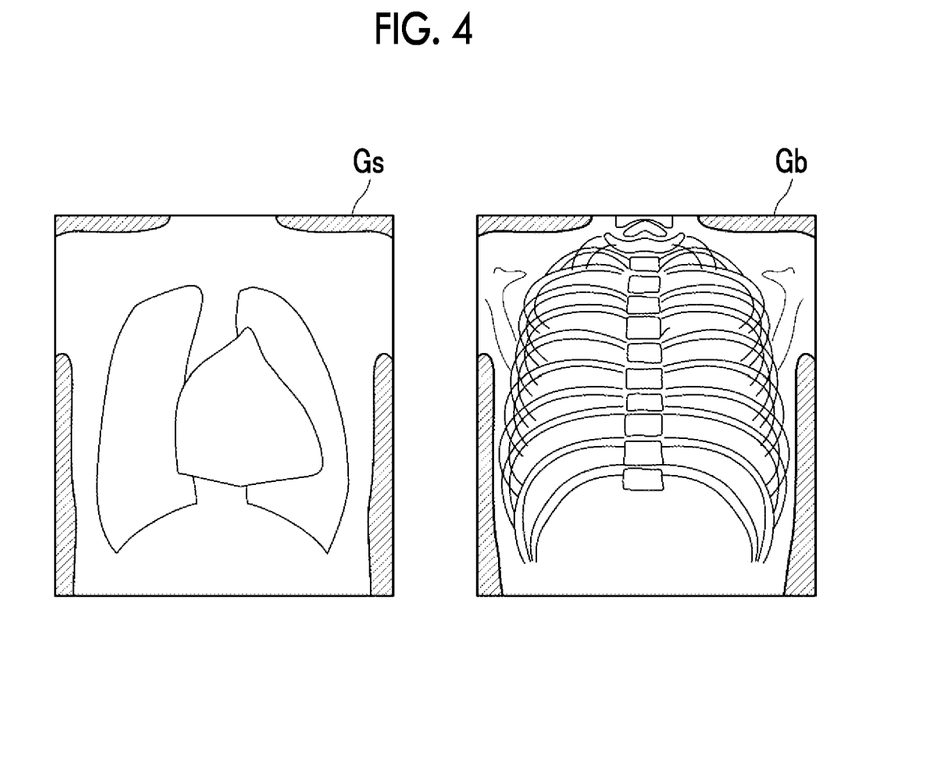
FIG. 4 is a diagram illustrating a soft part image and a bone part image.

The subtraction unit 35 derives the soft part image Gs obtained by extracting the soft part of the subject H and the bone part image Gb obtained by extracting the bone part, using the above-described Expressions (1) and (2). In this embodiment, first, the subtraction unit 35 performs the subtraction process of performing the weighting subtraction between the corresponding pixels of the first and second radiographic images G1 and G2, using the initial weighting coefficients α0 and β0 set by the initial weighting coefficient setting unit 34. Then, the subtraction process is performed using weighting coefficients αnew and βnew derived by the weighting coefficient derivation unit 36 as described below. FIG. 4 is a diagram illustrating the soft part image Gs and the bone part image Gb. As illustrated in FIG. 4, the soft part image Gs is obtained by extracting the soft part of the subject H. Further, the bone part image Gb is obtained by extracting the bone part of the subject H.

Figure 5:
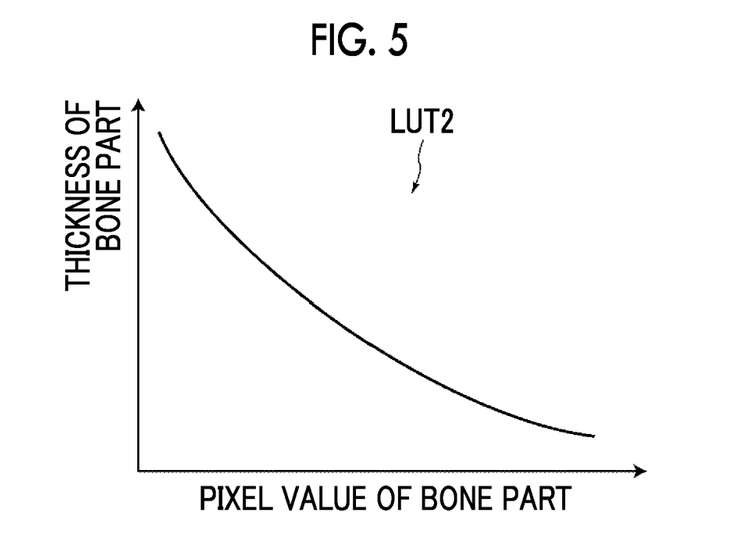
FIG. 5 is a diagram illustrating a table that defines a relationship between a pixel value of a bone part and the thickness of the bone part.

The weighting coefficient derivation unit 36 derives the new weighting coefficients αnew and βnew on the basis of the pixel value Gb(x, y) of the bone part included in the bone part image Gb. Here, the pixel value Gb(x, y) of the bone part corresponds to the thickness of the bone part of the subject H. Therefore, in this embodiment, a reference object simulating the bone parts having various thicknesses is imaged in advance to acquire a radiographic image of the reference object as a reference radiographic image. Then, a table that defines a relationship between the pixel value of the bone part and the thickness is derived in advance using a relationship between the pixel value of a reference object region in the reference radiographic image and the thickness of the reference object and is then stored in the storage 23. FIG. 5 is a diagram illustrating the table that defines the relationship between the pixel value of the bone part and the thickness of the bone part. A table LUT2 illustrated in FIG. 5 shows that, as the pixel value Gb(x, y) of the bone part becomes smaller (that is, brightness becomes higher), the thickness of the bone part becomes larger.

The weighting coefficient derivation unit 36 derives the thickness tb of the bone part in each pixel of the bone part image Gb from each pixel value Gb(x, y) of the bone part image Gb with reference to the table LUT2. In addition, since a region in which the bone part is not present in the bone part image Gb consists of only the soft part, the thickness tb of the bone part is 0. On the other hand, in the bone part image Gb, in the pixel in which the thickness tb of the bone part is not 0, the weighting coefficient derivation unit 36 subtracts the thickness tb of the bone part from the body thickness derived by the body thickness derivation unit 32 to derive the thickness ts of the soft part.

Figure 6:
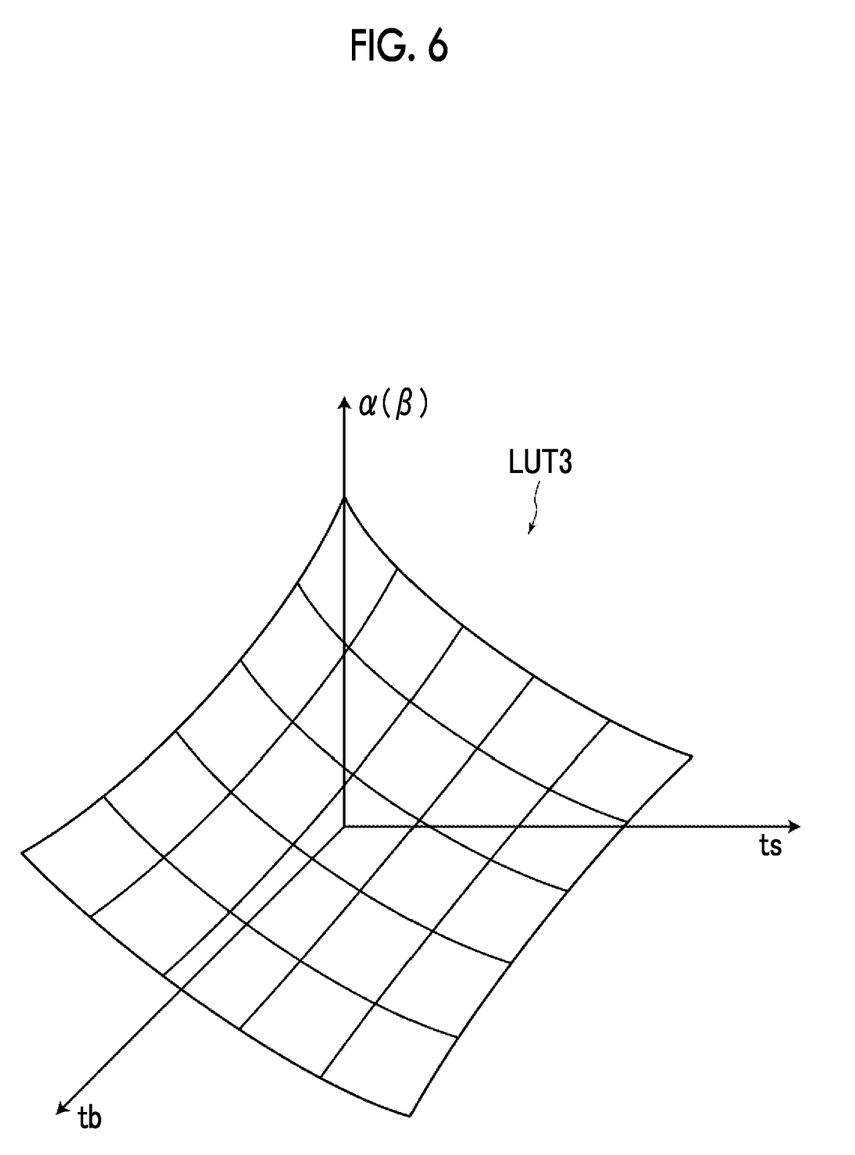
FIG. 6 is a diagram illustrating a table that defines a relationship among the thickness of the soft part, the thickness of the bone part, and a weighting coefficient.

As described above, the weighting coefficients α and β can be expressed as a function of the thickness ts of the soft part and the thickness tb of the bone part. In this embodiment, a table that defines the relationship among the thickness ts of the soft part, the thickness tb of the bone part, and the weighting coefficients α and β is stored in the storage 23. FIG. 6 is a diagram illustrating the table defining the relationship among the thickness ts of the soft part, the thickness tb of the bone part, and the weighting coefficients α and β. As illustrated in FIG. 6, a table LUT3 three-dimensionally represents the relationship among the thickness ts of the soft part, the thickness tb of the bone part, and the weighting coefficient α (or β). Here, in the table LUT3, as the thickness ts of the soft part and the thickness tb of the bone part become larger, the weighting coefficient α (or β) becomes smaller.

Further, in this embodiment, a plurality of tables LUT3 are prepared according to the energy distribution of the radiation used at the time of imaging and are stored in the storage 23. The weighting coefficient derivation unit 36 acquires information of the energy distribution of the radiation used at the time of imaging on the basis of the imaging conditions, reads out the table LUT3 corresponding to the acquired information of the energy distribution from the storage 23, and uses the table LUT3 to derive the weighting coefficient. Then, the weighting coefficient derivation unit 36 derives the new weighting coefficients αnew and βnew on the basis of the derived thickness tb of the bone part and the derived thickness ts of the soft part with reference to the table LUT3.

The subtraction unit 35 derives a new soft part image Gsnew and a new bone part image Gbnew on the basis of the new weighting coefficients αnew and βnew derived by the weighting coefficient derivation unit 36, using the above-described Expressions (1) and (2).

In addition, the new soft part image Gsnew and the new bone part image Gbnew may be stored as the final soft part image Gs and bone part image Gb in the storage 23 or may be displayed on the display unit 8. In this embodiment, the derivation of the weighting coefficients α and β and the subtraction process are repeatedly performed.

That is, the weighting coefficient derivation unit 36 derives a new thickness tbnew of the bone part on the basis of the pixel value of the bone part in the new bone part image Gbnew with reference to the table LUT2. Then, the weighting coefficient derivation unit 36 derives a difference Δtb between the new thickness tbnew of the bone part and the thickness tb of the bone part calculated in the previous process and determines whether or not the difference Δtb is less than a predetermined threshold value Th1. In a case in which the difference Δtb is equal to or greater than the threshold value Th1, the weighting coefficient derivation unit 36 derives a new thickness tsnew of the soft part from the new thickness tbnew of the bone part and derives further new weighting coefficients αnew and βnew on the basis of the new thickness tbnew of the bone part and the new thickness tsnew of the soft part with reference to the table LUT3.

The subtraction unit 35 performs the subtraction process using the further new weighting coefficients αnew and βnew to derive a further new bone part image Gbnew and a further new soft part image Gsnew.

Then, the weighting coefficient derivation unit 36 derives a further new thickness tbnew of the bone part on the basis of the further new bone part image Gbnew and derives the difference Δtb between the further new thickness tbnew of the bone part and the thickness tb of the bone part calculated in the previous process.

In this embodiment, the subtraction unit 35 and the weighting coefficient derivation unit 36 perform the subtraction process and the derivation of the weighting coefficients αnew and βnew until the difference Δtb derived by the weighting coefficient derivation unit 36 is less than the predetermined threshold value Th1.

Figure 7:
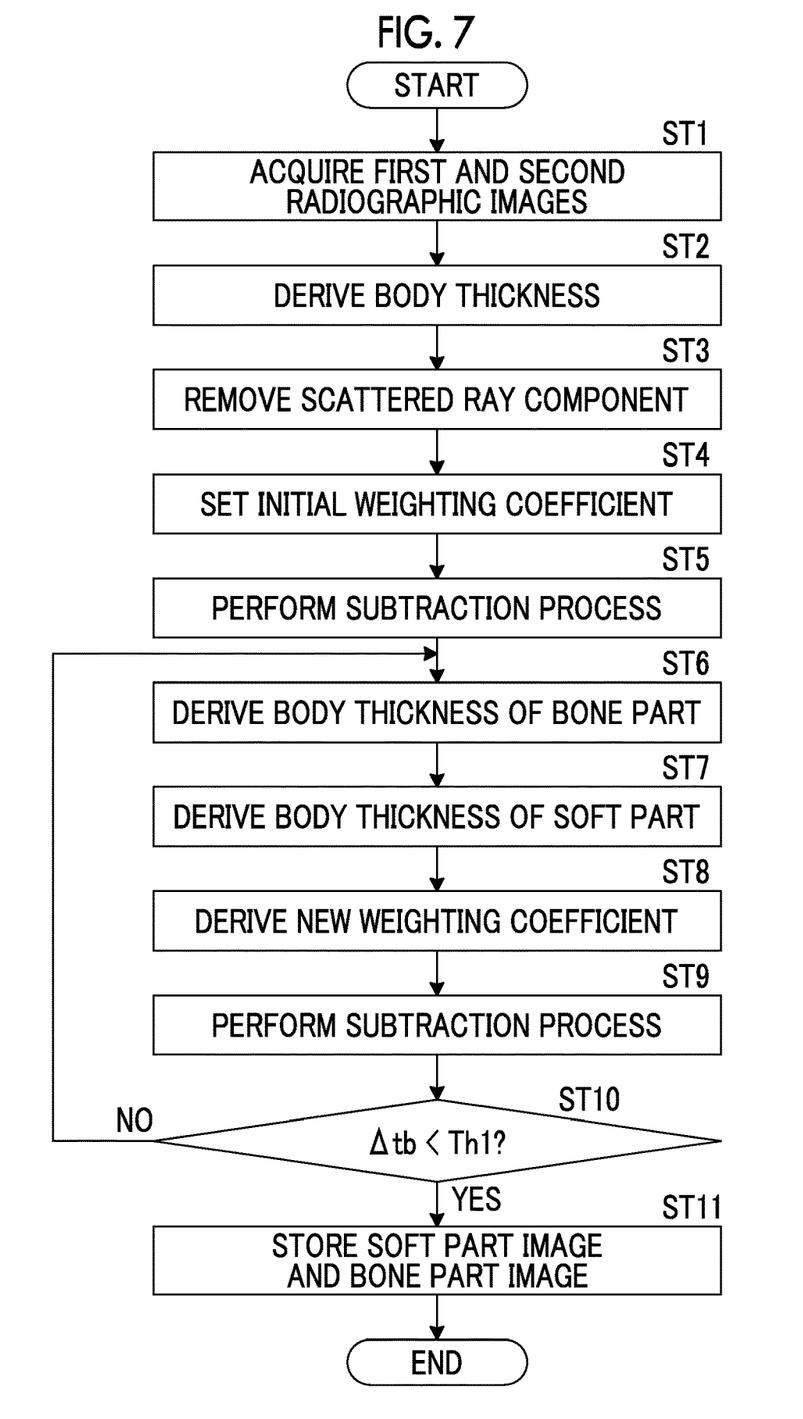
FIG. 7 is a flowchart illustrating a process performed in this embodiment.

Next, a process performed in this embodiment will be described. FIG. 7 is a flowchart illustrating the process performed in this embodiment. In addition, it is assumed that the first and second radiographic images G1 and G2 are acquired by imaging and are then stored in the storage 23. In a case in which an instruction to start the process is input from the input unit 9, the image acquisition unit 31 acquires the first and second radiographic images G1 and G2 from the storage 23 (Step ST1). Then, the body thickness derivation unit 32 derives the body thickness of the subject H (Step ST2), and the scattered ray removal unit 33 removes the scattered ray components from the first and second radiographic images G1 and G2 (Step ST3).

Then, the initial weighting coefficient setting unit 34 sets the initial weighting coefficients α0 and β0 in a case in which the subtraction process is performed (Step ST4). Then, the subtraction unit 35 performs the subtraction process on the basis of the initial weighting coefficients α0 and β0, using the above-described Expressions (1) and (2) (Step ST5). The soft part image Gs and the bone part image Gb are derived by this process.

Then, the weighting coefficient derivation unit 36 derives the thickness tb of the bone part on the basis of the bone part image Gb (Step ST6). In addition, the weighting coefficient derivation unit 36 subtracts the thickness tb of the bone part from the body thickness derived by the body thickness derivation unit 32 to derive the thickness ts of the soft part (Step ST7). Further, the weighting coefficient derivation unit 36 derives the new weighting coefficients αnew and βnew on the basis of the thickness tb of the bone part and the thickness ts of the soft part with reference to the table LUT3 (Step ST8).

Then, the subtraction unit 35 performs the subtraction process on the basis of the new weighting coefficients αnew and βnew using the above-described Expressions (1) and (2) (Step ST9). In this way, the new soft part image Gsnew and the new bone part image Gbnew are derived. Further, the weighting coefficient derivation unit 36 derives the new thickness tbnew of the bone part on the basis of the new bone part image Gbnew and determines whether or not the difference Δtb between the new thickness tbnew of the bone part and the thickness tb of the bone part calculated in the previous process is less than the predetermined threshold value Th1 (Step ST10).

In a case in which the determination result in Step ST10 is "No", the process returns to Step ST6. Then, the processes from Step ST6 to Step ST10 are repeated. In this way, the further new thickness tbnew of the bone part and the further new thickness tsnew of the soft part are derived, and the further new weighting coefficients αnew and βnew are derived. Then, the subtraction process is performed on the basis of the further new weighting coefficients αnew and βnew using the above-described Expressions (1) and (2) to derive a further new soft part image Gsnew and a further new bone part image Gbnew, and it is determined whether or not a further new difference Δtb is less than the threshold value Th1.

In a case in which the determination result in Step ST10 is "Yes", the last derived soft part image Gs and bone part image Gb are stored in the storage 23 (Step ST11), and the process ends. In addition, instead of or in addition to storing the soft part image Gs and the bone part image Gb, the soft part image Gs and the bone part image Gb may be displayed on the display unit 8.

Here, the composition of the human body includes a soft part and a bone part. In the bone part, the attenuation of radiation is greater than that in the soft part, and the radiation transmitted through the bone part shifts to the high energy side. Therefore, it is desirable to derive the weighting coefficients α and β in consideration of bone mass in the subject H in order to accurately separate the soft part and the bone part using the subtraction process.

According to this embodiment, the first and second radiographic images G1 and G2 are acquired by the radiation which has different energy distributions and has been transmitted through the subject H including the soft part and the bone part, and weighting subtraction is performed using the predetermined initial weighting coefficients α0 and β0 to derive the soft part image Gs and the bone part image Gb. Then, the new weighting coefficients αnew and βnew are derived on the basis of the pixel value of the bone part included in the bone part image Gb, and the subtraction process is performed, using the new weighting coefficients αnew and βnew, to derive the new soft part image Gsnew and the new bone part image Gbnew.

Here, the pixel value of the bone part reflects bone mass. Therefore, according to this embodiment, it is possible to derive the new weighting coefficients αnew and βnew in which bone mass has been reflected. Further, since the pixel value of the bone part is used, a relative weighting coefficient does not change even in a case in which the energy characteristics of the radiation source and the sensitivity characteristics of the radiation detector change. Therefore, according to this embodiment, the weighting coefficient can be derived without being affected by the deterioration of the imaging apparatus over time. As a result, it is possible to remove unnecessary structures in the soft part image Gs and the bone part image Gb derived by the energy subtraction process with high accuracy. That is, it is possible to remove the bone part in the soft part image Gs with high accuracy and to remove the soft part in the bone part image Gb with higher accuracy.

In addition, in the above-described embodiment, the body thickness derivation unit 32 derives the body thickness of the subject H. However, the present disclosure is not limited thereto. The body thickness may not be derived, but a predetermined average body thickness may be used. In this case, the initial weighting coefficient setting unit 34 sets the initial weighting coefficients α0 and β0 using the average body thickness.

Further, in the above-described embodiment, the scattered ray removal unit 33 removes the scattered ray components from the first and second radiographic images G1 and G2. However, the present disclosure is not limited thereto. For example, in a case in which the scattered ray removal grid is used at the time of imaging, it is possible to remove the scattered ray components from the first and second radiographic images G1 and G2. Therefore, in a case in which the scattered ray removal grid is used at the time of imaging, the subtraction process and the weighting coefficient derivation process may be performed without removing the scattered ray components from the first and second radiographic images G1 and G2.

Furthermore, in the above-described embodiment, the process is repeated until the determination result in Step ST10 is "Yes". However, the present disclosure is not limited thereto. The process may be repeated a predetermined number of times to derive the soft part image Gs and the bone part image Gb.

Further, in the above-described embodiment, the first and second radiographic images G1 and G2 are acquired by the one-shot method. However, the first and second radiographic images G1 and G2 may be acquired by a so-called two-shot method that performs imaging twice. Further, in the case of the two-shot method, the positions of the subject H included in the first and second radiographic images G1 and G2 are likely to deviate from each other due to the body movement of the subject H. Therefore, it is preferable to perform the process according to this embodiment after registering the positions of the subject in the first and second radiographic images G1 and G2. For example, the method disclosed in JP2011-255060A can be used as the registration process. For example, the method disclosed in JP2011-255060A generates a plurality of first band images and a plurality of second band images indicating structures having different frequency bands for each of first and second radiographic images G1 and G2, acquires the amount of positional deviation between the corresponding positions in the first band image and the second band image of the corresponding frequency band, and registers the first radiographic image G1 and the second radiographic image G2 on the basis of the amount of positional deviation.

Further, in the above-described embodiment, the energy subtraction process is performed using the radiographic images acquired in the system that captures the radiographic images of the subject using the first and second radiation detectors 5 and 6. However, the present disclosure may also be applied to a case in which the first and second radiographic images G1 and G2 are acquired using a storage phosphor sheet as the radiation detector. In this case, the first and second radiographic images G1 and G2 may be acquired by stacking two storage phosphor sheets, irradiating the storage phosphor sheets with radiation transmitted through the subject H such that the radiographic image information of the subject H is accumulated and recorded on each storage phosphor sheet, and photoelectrically reading the radiographic image information from each storage phosphor sheet. In addition, the two-shot method may also be used in a case in which the first and second radiographic images G1 and G2 are acquired using the storage phosphor sheets.

Figure 8:
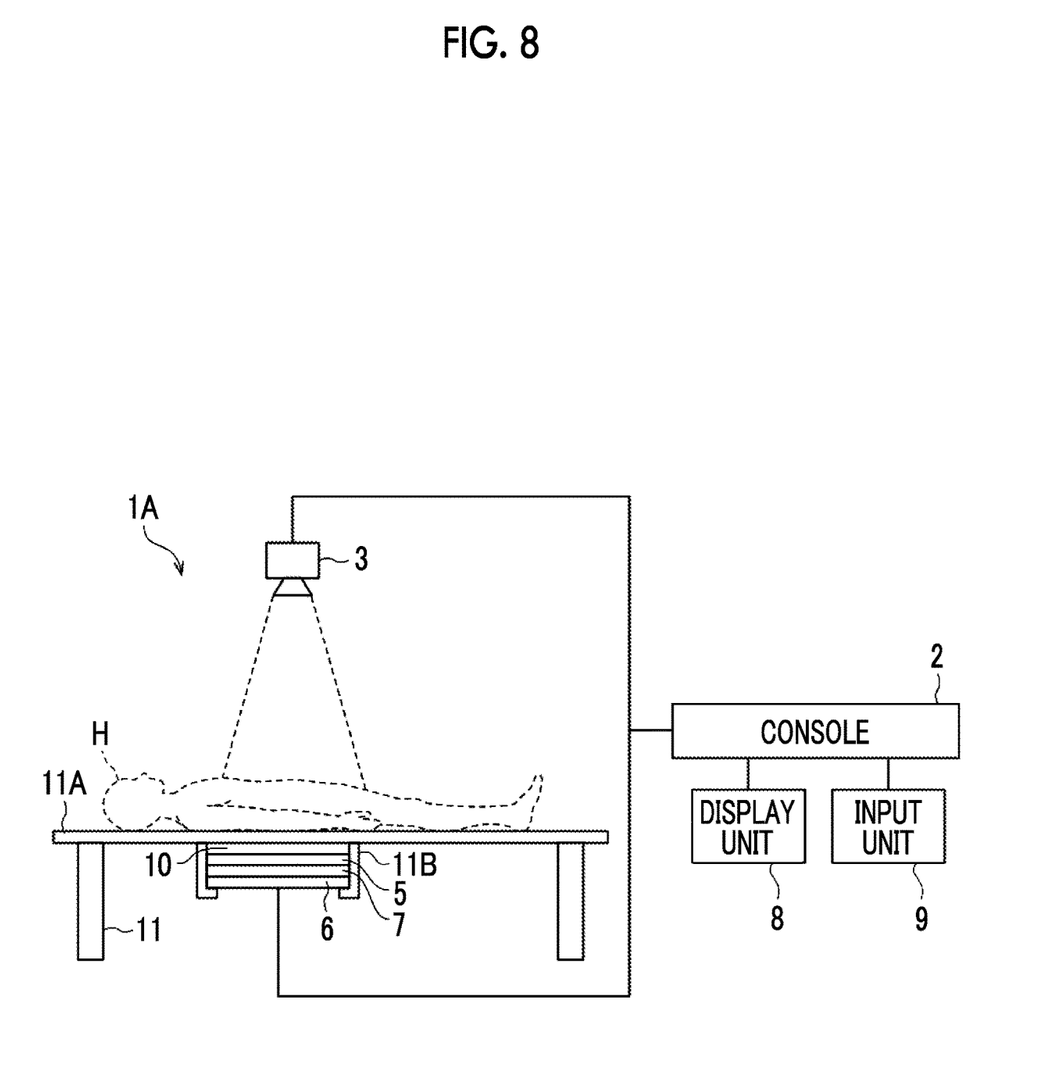
FIG. 8 is a diagram schematically illustrating a configuration of a radiography system to which an energy subtraction processing device according to another embodiment of the present disclosure is applied.

Furthermore, in the above-described embodiment, the image of the subject H in an upright position is captured. However, as illustrated in FIG. 8, the image of the subject H in a decubitus position may be captured. An imaging apparatus 1A in a radiography system illustrated in FIG. 8 is an imaging apparatus for acquiring a radiographic image of the subject H who lies on an imaging table 11 in a supine position. In the imaging apparatus 1A illustrated in FIG. 8, the first radiation detector 5, the radiation energy conversion filter 7, and the second radiation detector 6 are disposed in this order from the side closer to the radiation source 3. Further, a scattered ray removal grid 10 (hereinafter, simply referred to as a grid) for removing the scattered ray component scattered by the subject H in the radiation transmitted through the subject H is disposed between a top plate 11A of the imaging table 11 and the first radiation detector 5. The grid 10, the first radiation detector 5, the radiation energy conversion filter 7, and the second radiation detector 6 are attachably and detachably attached to the imaging table 11 by an attachment portion 11B that is provided on a lower surface of the top plate 11A of the imaging table 11.

In a case in which the imaging apparatus 1A illustrated in FIG. 8 is used, the top plate 11A of the imaging table 11 and the grid 10 are interposed between the subject H and the first radiation detector 5. In addition, in the imaging apparatus 1 illustrated in FIG. 1 and the imaging apparatus 1A illustrated in FIG. 8, in some cases, air is interposed between the subject H and the first radiation detector 5 at the time of imaging. In this case, the first radiation detector 5 is irradiated with the radiation transmitted through the subject H, the top plate 11A, the grid 10, and an air layer in this order. Here, objects, such as the top plate 11A, the grid 10, and air, have unique radiation characteristics. Therefore, since the radiation is transmitted through the objects, the quality of the primary ray component and the scattered ray component transmitted through the subject H changes depending on the radiation characteristics of the objects. In addition, even in a case in which the grid 10 is used, it is difficult to completely remove the scattered rays. Therefore, the radiation transmitted through the subject H includes a scattered ray component. For this reason, in this embodiment, it is preferable to consider the radiation characteristics of the objects interposed between the subject H and the first radiation detector 5 in a case in which the estimation of the body thickness distribution using the first radiographic image G1 and the removal of the scattered ray component are performed.

Specifically, the primary ray transmittance and the scattered ray transmittance of radiation corresponding to the types of objects interposed between the subject H and the first radiation detector 5 are generated as, for example, a table in advance according to various imaging conditions and the body thickness distribution of the subject H and are stored in the storage 23. Then, in a case in which the body thickness derivation unit 32 and the scattered ray removal unit 33 perform the estimation of the body thickness distribution of the subject H and the removal of the scattered rays, the radiation characteristics of the objects corresponding to the body thickness distribution, that is, the primary ray transmittance and the scattered ray transmittance of radiation are acquired with reference to the table. In addition, the scattered ray removal unit 33 acquires an estimated primary ray image and an estimated scattered ray image, using the acquired radiation characteristics, imaging conditions, and body thickness distribution and adds the estimated primary ray image and the estimated scattered ray image to generate an estimated image. Further, the body thickness derivation unit 32 and the scattered ray removal unit 33 repeatedly perform the generation of the estimated image and the correction of the body thickness distribution until the difference between the estimated image and the first radiographic image G1 satisfies a predetermined end condition. Then, the body thickness derivation unit 32 derives, as the body thickness of the subject H, a body thickness distribution in a case in which the end condition is satisfied. Furthermore, the scattered ray removal unit 33 subtracts the estimated scattered ray image in a case in which the body thickness distribution satisfying the end condition is acquired from the first radiographic image G1 to remove the scattered ray components from the first radiographic image G1. Therefore, it is possible to remove the scattered ray components from the first radiographic image G1 in consideration of the radiation characteristics of the objects interposed between the subject H and the first radiation detector. In addition, similarly, it is possible to remove the scattered ray components from the second radiographic image G2.

Further, the radiation in the above-described embodiment is not particularly limited. For example, α-rays or γ-rays can be applied in addition to the X-rays.

Furthermore, in the above-described embodiment, for example, the following various processors can be used as a hardware structure of processing units performing various processes, such as the image acquisition unit 31, the body thickness derivation unit 32, the scattered ray removal unit 33, the initial weighting coefficient setting unit 34, the subtraction unit 35, and the weighting coefficient derivation unit 36 of the console 2 which is the energy subtraction processing device. The various processors include, for example, a CPU which is a general-purpose processor executing software (program) to function as various processing units as described above, a programmable logic device (PLD), such as a field programmable gate array (FPGA), which is a processor whose circuit configuration can be changed after manufacture, and a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system on chip (SoC). As such, various processing units are configured by using one or more of the various processors as a hardware structure.

Furthermore, specifically, an electric circuit (circuitry) obtained by combining circuit elements, such as semiconductor elements, can be used as the hardware structure of the various processors.

What is claimed is:

1. An energy subtraction processing device comprising at least one processor, wherein the processor is configured to:
    acquire two radiographic images based on radiation which has different energy distributions and has been transmitted through a subject including a soft part and a bone part;
    perform weighting subtraction using a predetermined initial weighting coefficient between corresponding pixels of the two radiographic images to derive a soft part image obtained by extracting the soft part of the subject and a bone part image obtained by extracting the bone part of the subject;
    derive a new weighting coefficient on the basis of a pixel value of the bone part included in the bone part image; and
    perform the weighting subtraction on the two radiographic images using the new weighting coefficient to derive a new soft part image and a new bone part image.

2. The energy subtraction processing device according to claim 1,
    wherein the processor is configured to derive the new weighting coefficient on the basis of a predetermined relationship between the pixel value of the bone part and the weighting coefficient.

3. The energy subtraction processing device according to claim 1,
    wherein the processor is configured to correct the new weighting coefficient on the basis of a pixel value of a bone part included in the new bone part image to derive a further new weighting coefficient, perform the weighting subtraction using the further new weighting coefficient to derive a further new soft part image and a further new bone part image, and repeat the derivation of the further new weighting coefficient based on the new bone part image and the derivation of the further new soft part image and the further new bone part image based on the new weighting coefficient to derive the weighting coefficient, the soft part image, and the bone part image.

4. The energy subtraction processing device according to claim 1, wherein the processor is further configured to:

remove scattered ray components included in the two radiographic images, and perform the weighting subtraction on the basis of the two radiographic images from which the scattered ray components have been removed.

5. The energy subtraction processing device according to claim 4, wherein the processor is configured to remove the scattered ray components included in the two radiographic images on the basis of radiation characteristics of an object interposed between the subject and detectors that acquire the two radiographic images.

6. The energy subtraction processing device according to claim 1, wherein the two radiographic images are acquired by two detectors, wherein the two detectors are superimposed on each other and irradiated with the radiation transmitted through the subject at the same time.

7. The energy subtraction processing device according to claim 1, wherein the processor is further configured to set the initial weighting coefficient on the basis of a body thickness of the subject.

8. The energy subtraction processing device according to claim 7, wherein the processor is further configured to derive the body thickness of the subject.

9. An energy subtraction processing method comprising:

acquiring two radiographic images based on radiation which has different energy distributions and has been transmitted through a subject including a soft part and a bone part;

performing weighting subtraction using a predetermined initial weighting coefficient between corresponding pixels of the two radiographic images to derive a soft part image obtained by extracting the soft part of the subject and a bone part image obtained by extracting the bone part of the subject;

deriving a new weighting coefficient on the basis of a pixel value of the bone part included in the bone part image; and performing the weighting subtraction on the two radiographic images using the new weighting coefficient to derive a new soft part image and a new bone part image.

10. A non-transitory computer-readable storage medium that stores an energy subtraction processing program that causes a computer to perform:

a procedure of acquiring two radiographic images based on radiation which has different energy distributions and has been transmitted through a subject including a soft part and a bone part;

a procedure of performing weighting subtraction using a predetermined initial weighting coefficient between corresponding pixels of the two radiographic images to derive a soft part image obtained by extracting the soft part of the subject and a bone part image obtained by extracting the bone part of the subject;

a procedure of deriving a new weighting coefficient on the basis of a pixel value of the bone part included in the bone part image; and a procedure of performing the weighting subtraction on the two radiographic images using the new weighting coefficient to derive a new soft part image and a new bone part image.

* * * * *